US006547790B2

(12) United States Patent
Harkey, III et al.

(10) Patent No.: US 6,547,790 B2
(45) Date of Patent: Apr. 15, 2003

(54) ORTHOPAEDIC ROD/PLATE LOCKING MECHANISMS AND SURGICAL METHODS

(75) Inventors: Haynes Louis Harkey, III, Ridgeland, MS (US); Bradford Currier, Rochester, MN (US); David M. Selvitelli, Wellesley, MA (US); Martin A. Reynolds, Mansfield, MA (US); Thomas V. Doherty, Foxboro, MA (US)

(73) Assignee: Depuy Acromed, Inc., Raymham, MA (US)

( * ) Notice: Subject to any disclaimer, the term of this patent is extended or adjusted under 35 U.S.C. 154(b) by 7 days.

(21) Appl. No.: 09/836,445

(22) Filed: Apr. 17, 2001

(65) Prior Publication Data

US 2002/0049446 A1 Apr. 25, 2002

Related U.S. Application Data

(63) Continuation-in-part of application No. 09/633,057, filed on Aug. 8, 2000.

(51) Int. Cl.$^7$ .............................................. A61B 17/56
(52) U.S. Cl. .............................. 606/61; 606/60; 606/70
(58) Field of Search .............................. 606/61, 74, 73, 606/60, 70, 71, 72

(56) References Cited

U.S. PATENT DOCUMENTS

| 4,299,212 A | 11/1981 | Goudfrooy .................. 128/92 |
| 4,815,453 A | 3/1989 | Cotrel .......................... 128/69 |
| 4,841,959 A | 6/1989 | Ransford .................... 128/192 |
| 4,887,595 A | 12/1989 | Heinig et al. ................. 606/61 |
| 5,024,213 A | 6/1991 | Asher et al. ................. 128/69 |
| 5,127,912 A | 7/1992 | Ray et al. ..................... 606/61 |
| 5,129,900 A | 7/1992 | Asher et al. ................. 606/61 |
| 5,176,680 A | 1/1993 | Vignaud et al. ............. 606/61 |
| 5,190,543 A | 3/1993 | Schlapfer .................... 606/61 |
| 5,217,461 A | 6/1993 | Asher et al. ................. 606/61 |
| 5,257,993 A | 11/1993 | Asher et al. ................. 606/61 |

(List continued on next page.)

OTHER PUBLICATIONS

"The CerviFix System: Including the StarLock Components," Synthes product literature.
"Occipitocervical Rod: Occipitocervical Osteosynthesis," Cotrel–Dubousset Instrumentation product literature.
Uppsala, S.E., "The Cross–Cervical Rod Spinal System: A Multi–Option Posterior Fixation Device for the Cervical Spine," NordOpedic AB (Sept. 1, 1996).

*Primary Examiner*—Pedro Philogene
(74) *Attorney, Agent, or Firm*—Nutter, McClennen & Fish LLP

(57) ABSTRACT

An orthopaedic method and anchor assemblies for anchoring a linkage such as a rod or cable used for fixation or reduction. One assembly includes an anchor plate and a slotted anchor bolt that captures the plate in a one-piece assembly for convenient installation. The base of the anchor bolt lies below the plate, and a cap or nut tightens down to secure a linking member, e.g., a rod or cable, in the slot, simultaneously clamping the bolt to fix both its position and its orientation on the plate. One occipital plate has lateral arms that hold the anchor bolts, and a Y-shaped embodiment is mounted in an inverted orientation to position the anchor bolts well down in soft tissue for more effective wound closure. A cable connector is used together with an anchor plate, vertebra anchor screws and fixation rods to secure ends of a cable at the level of one or more vertebrae, providing a versatile and highly stable system for alignment, fixation and fusing of the cervical and thoracic spine. The cable connectors have an open-sided channel that fits onto and securely clamps to an already-positioned fixation rod, with an eyelet or other structure providing a rigid and fixed securing point for a cable that is threaded about the vertebrae under tension. Methods of fixation are described.

24 Claims, 11 Drawing Sheets

U.S. PATENT DOCUMENTS

| | | | | |
|---|---|---|---|---|
| 5,261,912 A | 11/1993 | Frigg | | 606/61 |
| 5,306,275 A | 4/1994 | Bryan | | 606/61 |
| 5,312,404 A | 5/1994 | Asher et al. | | 606/61 |
| 5,360,429 A | 11/1994 | Jeanson et al. | | 606/61 |
| 5,443,467 A | 8/1995 | Biedermann et al. | | 606/65 |
| 5,490,822 A | 2/1996 | Biedermann | | 602/16 |
| 5,498,264 A | 3/1996 | Schlapfer et al. | | 606/72 |
| 5,501,684 A | 3/1996 | Schlapfer et al. | | 606/73 |
| 5,507,745 A | 4/1996 | Logroscino et al. | | 606/61 |
| 5,520,689 A | 5/1996 | Schlapfer et al. | | 606/61 |
| 5,534,001 A | 7/1996 | Schlapfer et al. | | 606/61 |
| 5,542,946 A | 8/1996 | Logroscino et al. | | 606/61 |
| 5,545,164 A | 8/1996 | Howland | | 606/61 |
| 5,545,165 A | 8/1996 | Biedermann et al. | | 606/61 |
| 5,591,167 A | 1/1997 | Laurain et al. | | 606/61 |
| 5,593,408 A | 1/1997 | Gayet et al. | | 606/61 |
| 5,601,552 A | 2/1997 | Cotrel | | 606/61 |
| 5,601,553 A | 2/1997 | Trebing et al. | | 606/61 |
| 5,615,965 A | 4/1997 | Saurat et al. | | 403/24 |
| 5,651,789 A | 7/1997 | Cotrel | | 606/61 |
| 5,672,176 A | 9/1997 | Biedermann et al. | | 606/61 |
| 5,676,640 A | 10/1997 | Biedermann | | 602/26 |
| 5,702,395 A | 12/1997 | Hopf | | 606/61 |
| 5,702,452 A | 12/1997 | Argenson et al. | | 623/17 |
| 5,702,453 A | 12/1997 | Rabbe et al. | | 623/17 |
| 5,713,898 A | * 2/1998 | Stucker et al. | | 606/60 |
| 5,716,355 A | 2/1998 | Jackson et al. | | 606/61 |
| 5,716,356 A | 2/1998 | Biedermann et al. | | 606/61 |
| 5,725,527 A | 3/1998 | Biedermann et al. | | 606/61 |
| 5,741,255 A | 4/1998 | Krag et al. | | 606/61 |
| 5,741,258 A | 4/1998 | Klaue et al. | | 606/70 |
| 5,743,907 A | 4/1998 | Asher et al. | | 606/61 |
| 5,743,911 A | 4/1998 | Cotrel | | 606/61 |
| 5,810,823 A | 9/1998 | Klaue et al. | | 606/69 |
| 5,814,046 A | 9/1998 | Hopf | | 606/61 |
| 5,873,878 A | 2/1999 | Harms et al. | | 606/61 |
| 5,879,352 A | 3/1999 | Filoso et al. | | 606/62 |
| 5,899,906 A | 5/1999 | Schenk | | 606/73 |
| 5,928,233 A | 7/1999 | Apfelbaum et al. | | |
| 5,961,517 A | 10/1999 | Biedermann et al. | | 606/61 |
| 5,976,135 A | * 11/1999 | Sherman et al. | | 606/61 |
| 5,976,141 A | 11/1999 | Haag et al. | | 606/72 |
| 5,993,449 A | * 11/1999 | Schlapfer et al. | | 606/60 |
| 6,027,533 A | 2/2000 | Olerud | | 623/17 |
| 6,063,090 A | 5/2000 | Schlapfer | | 606/61 |
| 6,086,590 A | 7/2000 | Margulies et al. | | |
| 6,099,528 A | 8/2000 | Saurat | | 606/61 |
| 6,102,912 A | 8/2000 | Cazin et al. | | 606/61 |
| 6,106,526 A | 8/2000 | Harms et al. | | 606/61 |
| 6,139,548 A | 10/2000 | Errico | | 606/61 |
| 6,146,382 A | 11/2000 | Hurlbert | | 606/61 |
| 6,168,597 B1 | 1/2001 | Biedermann et al. | | 606/73 |
| 6,179,841 B1 | 1/2001 | Jackson | | 606/73 |
| 6,187,005 B1 | * 2/2001 | Brace et al. | | 606/61 |
| 6,187,009 B1 | 2/2001 | Herzog et al. | | 606/75 |

* cited by examiner

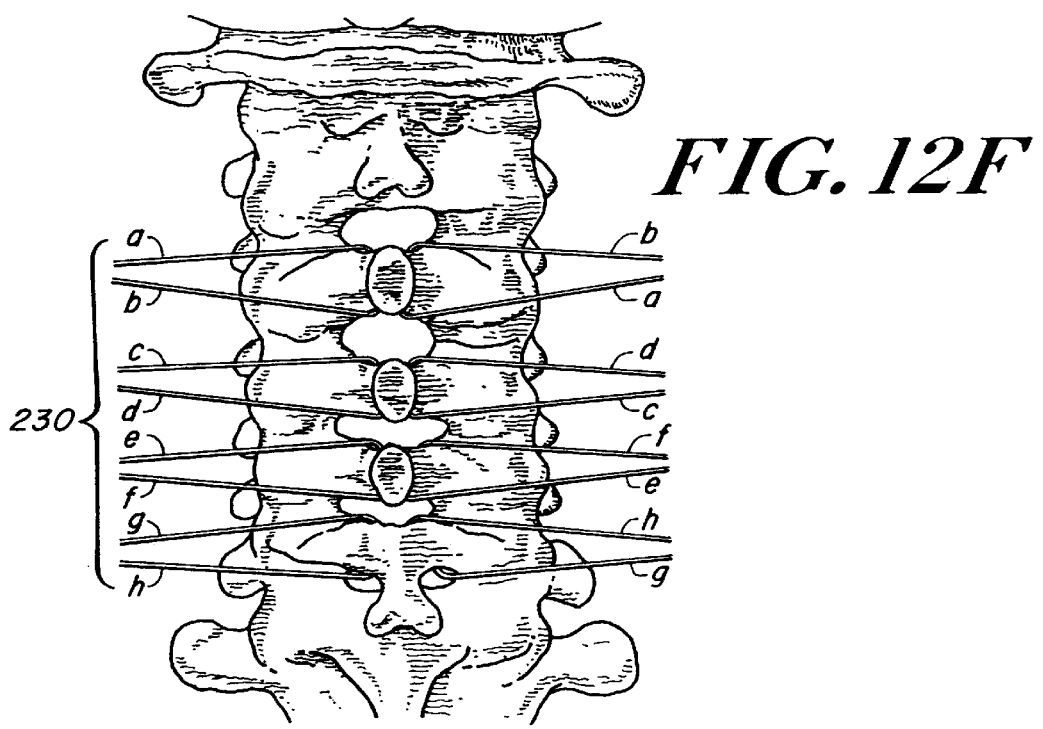
FIG. 12F
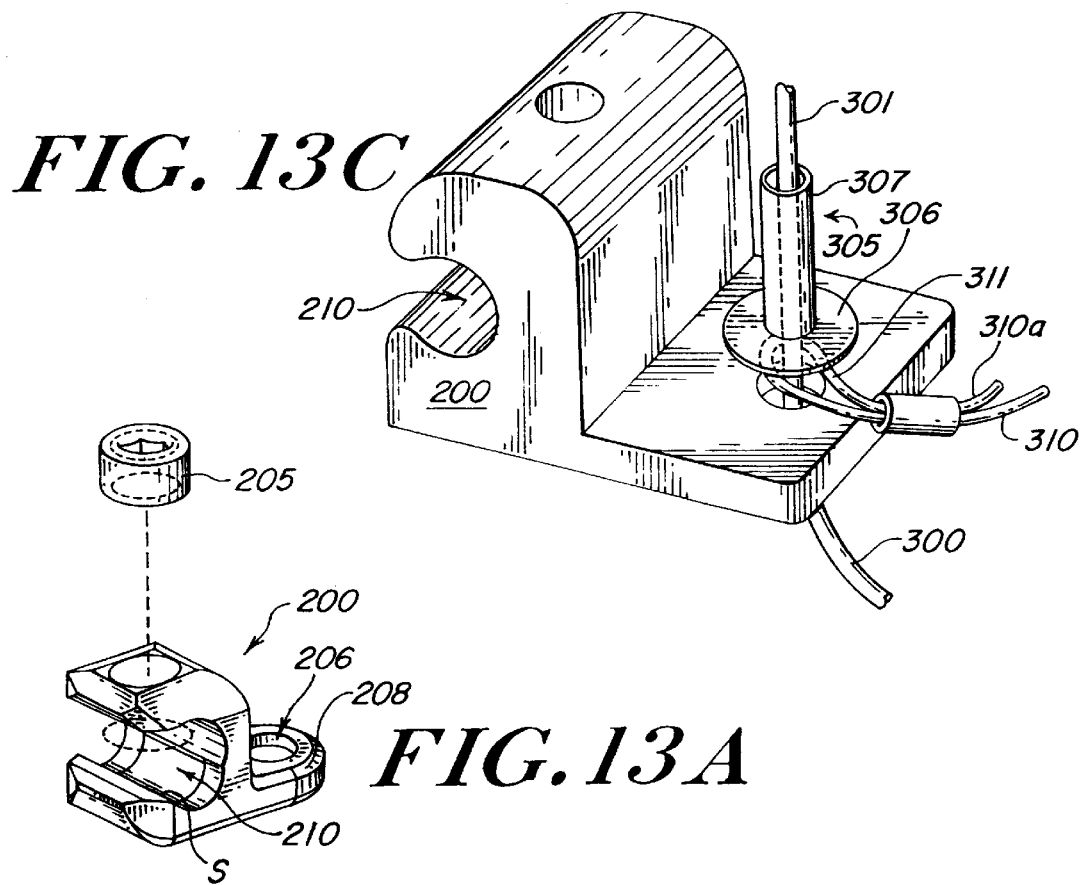
FIG. 13C
FIG. 13A

ORTHOPAEDIC ROD/PLATE LOCKING MECHANISMS AND SURGICAL METHODS

REFERENCE TO RELATED APPLICATIONS

This application is a continuation-in-part of prior U.S. patent application Ser. No. 09/633,057 filed on Aug. 8, 2000 for Orthopaedic Rod/Plate Locking Mechanism.

BACKGROUND

The present invention relates to fixation devices used in orthopaedic surgery and particularly to devices used for the reduction of fractures or the positioning of bones by means of a plate attached to a bone or bone fragment in one region and secured to a rod which attaches to a cable, wire, plate or screw fastened in another region. The rod thus attaches between two bone regions for effecting stabilization, positioning, reduction or fixation of the bones.

A number of such mechanisms are known, among which should be mentioned the Harms T-plate which employs a split or slotted bolt, the head of which slides in a slot of a plate that is attached to a bone or bone fragment. The plate accepts the slotted bolt from the bottom and has several channels or grooves extending in different directions in the plate to allow positioning and alignment of the bolt along any one of the distinct channels. In use, a connecting rod fits through the slotted bolt and is captured by a nut which, when tightened, locks the bolt in its position in the channel, and secures the rod in the slot. In general, the system employs a slotted bolt with a square flange at its base so that each of the channels defines orientation of the rod-receiving slot of the outwardly protruding portion of the bolt. The plate thus provides a range of linear positions along several discrete lines, each at a fixed angular orientation, for the rod anchor point.

In addition to such plates, for posterior cervical fixation there also exist a number of eye screws that screw directly into the bone at a single fixed position. In these screws, the eye structure generally is an open slot or other rod-receiving open form adapted to receive the rod therein before being closed by a cap. The cap may be a conventional threaded locking nut, or in some constructions may be a dovetailed cap segment which slides in and wedges against the rod to secure the rod while closing the receiving slot at its open end. Such eye screws may also, in some constructions, be employed to secure a plate to the bone in addition to gripping the stabilization rod. When so used, the plate serves to strengthen the attachment and distribute the stresses coupled by the anchoring screw.

One variant of a rod-receiving fixation screw is the Moss-Miami polyaxial screw, as shown in U.S. Pat. No. 5,672,176. In that device, the screw has a spherical head. A slotted rod-holding cap structure having a conically tapering inner surface fits about the outside of the spherical head in the manner of a ball and socket joint. The rod-holding cap structure is internally threaded and is provided with a number of shaped packing or pressure-bearing inserts with an overall structure that tightens about the spherical screw head as the cap is drawn upward forcing the head down the cone angle. The cap may be rotated before tightening on the spherical head, so this clamping connection allows the rod-holding member to be bolted down and fixed with its slot oriented at an arbitrary angle in rotation about the axis of the screw. The rod fits through the slot in the holding cap structure and is secured by tightening a bolt into the threaded cap. The unit comes as a pre-assembled device with the packing or pressure-bearing members positioned internally about the ball end of the screw and held by swaging part way up the cap. Tightening of the cap against the rod then draws the conical outer holding body upward against the ball, fixing the slot orientation with the rod in position.

When the underlying bone has sufficient integrity, such individual eye screws offer great flexibility in rod orientation in one plane. Also, when a bone plate secured by multiple screws is necessary, the Harms plate offers a range of clamping point translational positions with a discrete set of angular orientations for connecting a cable, fixation rod or reduction rod. However, each of these systems has its own limitations as to convenience, or as to the range of position or orientation, or to the degree of loading that it may accommodate. In addition, the various plates, and screw heads or cap structures may present bulky or irregular profiles that pose obstacles to effective anchoring or surgical closure in some locations.

Accordingly, it would be desirable to provide a bone plate and rod junction system of adjustable angulation.

It would also be desirable to provide a multi-axis rod connection that is freely positionable along a slotted plate.

It would also be desirable to provide a multi-axis rod connection in which the components are pre-assembled to be installed as a unit during surgery.

It would also be desirable to provide an improved anchor plate structure.

It would also be desirable to provide improved methods of spinal fixation embodying mechanical anchor, rod and cabling units effective to fix and secure the spine.

SUMMARY OF THE INVENTION

One or more of the foregoing desirable ends are achieved in accordance with the present invention by a rod junction mechanism including a slotted bolt, a rod support platform that fits over the bolt, and a nut which tightens down to secure a rod in the slot on the support platform. The base of the bolt is configured to ride in a slot or a counter-bored aperture or channel in a plate or offset tab and is round so it rotates freely in the plate, while the support platform has the form of a generally annular and thick washer that lies over the base of the bolt to sandwich the plate therebetween and clamp firmly in position. The washer has an upper surface possessing a rounded groove on which the rod lies and a lower surface with a step collar that extends within and buttresses the walls of the opening in the plate. The plate is sandwiched between the base of the bolt and the support platform, distributing stress over a wide area while providing a strong anvil to support the rod.

In one embodiment the support platform has lateral openings that extend radially to a depth close to, but not through, its radially inner wall surface so as to leave a thinned wall portion. The bolt is placed through the plate and the platform is swaged to the bolt at the thinned wall portion so as to capture the bone plate therebetween, providing a single-piece assembly for convenience of handling and installation. In this configuration, the bolt may move freely within the bone plate opening as a captive assembly, easing placement during surgery by keeping all the components together. The swaging fixes alignment of the groove of the support plate form along the direction of the slot of the bolt, while leaving both pieces free to rotate, and when the plate opening is a slot, to translate along the slot of the bone plate. Rather than swaging, a preferred embodiment implements a one-piece assembly by providing a circumferential groove and a corresponding ridge on the bolt shaft and the support platform, to function as a snap ring and retain the two parts together during handling and use. In use, once the rod is positioned in the upwardly extending bolt slot, a locking nut or cap, which may be of conventional type, threads onto the bolt. The nut forces the rod against the support platform which, in turn, pushes downward against the bone plate while the nut also pulls the bolt upward, forcing the bolt base flange against the bottom of the plate. The bottom surface of the support platform, the plate-facing surface of the bolt flange, and/or the surface(s) of the plate may be roughened or toothed so as to enhance gripping and increase resistance to rotational or lateral movement of the bolt once the rod has been positioned and the nut torqued down.

A plate for occipital fixation has the shape of a T or a Y, with anchor screw apertures along a central portion, and a rod-clamping anchor structure positioned on each lateral arm or branch of the plate. The Y-plate embodiment may be inverted, such that the plate attaches along the midline of the skull below the external occipital protuberance, and positions the rod clampimg structures more effectively below soft tissue, facilitating surgical wound closure.

Systems and methods of spinal fixation provide fixation rods secured to anchors on the occipital plate and on one or more vertebrae of the cervical and/or thoracic spine, and may include one or more cables fixed by cable connectors that clamp to the rods.

BRIEF DESCRIPTION OF THE DRAWINGS

These and other features of the invention will be understood from the description herein, taken together with drawings of illustrative embodiments, wherein

FIG. 12F illustrates cable layout according to one embodiment; and

DETAILED DESCRIPTION

Figure 1:
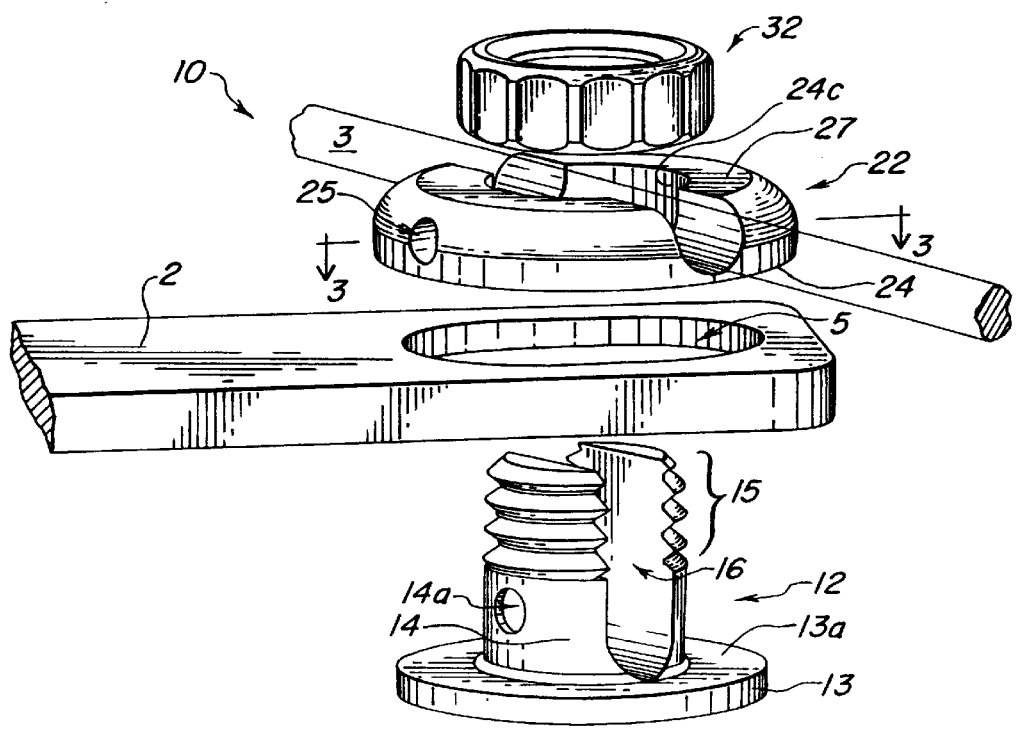
FIG. 1 shows an exploded perspective view of the rod junction system of the present invention.

FIG. 1 shows an exploded perspective view of one embodiment of the rod junction system 10 of the present invention. As shown, in this embodiment, the invention is comprised of a plate 2 through which a slotted bolt 12 fits, with a rod-contacting support platform 22 or support collar fitted over the bolt 12, and a nut or cap 32 fitted onto the end of the bolt to secure the rod. Rod 3 is shown in phantom for purposes of illustration. The aperture 5 in the plate 2 may be a simple round hole, an elongated but closed-ended slot as illustrated, or an open-ended slot of the type known in the prior art that allows the bolt 12 to be moved to various positions along the plate length. Furthermore, the plate may take any of a number of configurations of the various shapes commonly used in orthopaedic fixation. That is, the plate may be generally planar, and shaped like a strip, an L-, T-, V-, Y- or other shape; or it may be a short tab, adapted to extend laterally from a bone fixation point to position the bolt 12 at an offset or out-of-plane position for clamping the rod 3. It may also be bent or curved out-of-plane to fit a curved bone surface, and may be installed in various orientations. In one embodiment, the assembly is used with a plate 2 that has the contour of an occipital bone fixation plate, and the bolts 12 are positioned at both sides of a center line for securing two fixation rods extending in parallel to the spine. Exemplary T-shaped, Y-shaped and inverted-Y plates and methods of installation are described further below.

Figure 3:
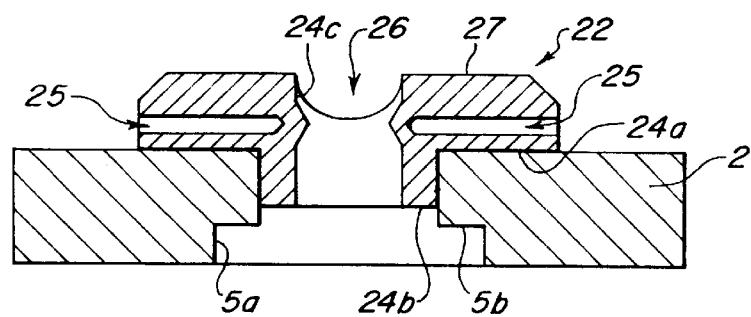
FIG. 3 shows a cross-sectional view through the system of FIG. 1.

As shown in FIG. 3, the hole or slot 5 of plate 2 is counter-bored or milled to a larger opening 5a, so that the base 13 of the slotted bolt fits up in and is recessed from the level of the bottom surface of the plate 2, against a step or thrust face 5b. Thus, the opening 5 may be a counter-bored hole or elongated hole, or one of several step-walled slots. As further shown in FIG. 1, the bolt 12 includes a shank portion 14 extending from the base 13, and a threaded shaft portion 15 extending above the shank. A U-shaped slot 16 runs the length of the threaded shaft 15 and preferably extends through at least a portion of the shank 14. Furthermore the base 13 in the illustrated embodiment is generally disk-shaped or radially symmetric in that it allows the bolt 12 to rotate freely in the hole or slot of plate 2 through one full revolution. The base 13 is considerably wider than the hole 5, so the bolt 12 cannot be pulled through the plate.

On the other side of the plate 2, the support platform 22 or thrust collar fits around the threaded shaft of the bolt and has a shallow yoke or transverse groove 26 (FIG. 3) formed in its top surface 27. In use, groove 26 aligns with the slot 16 of the bolt 12, and forms a bearing or seating surface on which the rod 3 rests. The support platform 22 is formed as an annular washer that functions as a support anvil for the rod 3 and also as a collar or sleeve about the bolt 12. It thus operates together with the bolt to reinforce the apertured plate 2 and effectively sandwich the plate between the base 13 of the bolt and the platform 22 itself.

As further shown in the vertical sectional view of FIG. 3 taken in a diametral plane of the bolt transverse to the direction of the slot, for this purpose the platform 22 has a lower surface 24 comprised of a washer-like body portion with an outer peripheral surface in a band 24a that rests on the top of the plate 2, and an inner annular portion 24b which extends into the plate opening 5 and forms a collar or reinforcement sleeve within the opening 5 of the plate 2. In this embodiment, a pair of radially directed holes 25, of which one is visible in FIG. 1, extend inward from the circumferentially outer wall of the platform 22 to a depth close to its radially inner surface 24c. As best seen in FIG. 3, the holes 25 serve as access holes to permit swaging the remaining thin-walled inner collar portion of the support platform member 22 to the bolt 12 while the plate 2 is captured between the bolt base 13 and the platform 22, so that the entire assembly forms a single unit loosely held together and freely movable without danger of losing the parts during handling prior to installation.

In the embodiment illustrated in FIGS. 1 and 2, the components are dimensioned so that the platform 22 is swaged to the shank 14 of the bolt below the threaded region 15, and at positions transverse to the axis of the slot 26. For this purpose cross-holes or recesses 14a are preferably drilled or otherwise formed in the shank at positions corresponding to the deformed swaging of the inner wall. Like the base 13 of the bolt 12, the platform 22 extends radially outward beyond the aperture 5 so that when it is swaged together with the bolt, the plate 2 is captured therebetween while the bolt and support platform assembly 12, 22 may rotate freely together as a unit to any angular position in a plane transverse to the axis of the bolt shaft. As shown, the unthreaded shank portion 14 of the bolt extends for a length roughly equal to the thickness of plate 2 and platform 22, and the threaded portion of the shaft 15 extends for a sufficient further length to allow the nut 32 to clamp the rod and bolt assembly together.

Figure 2:
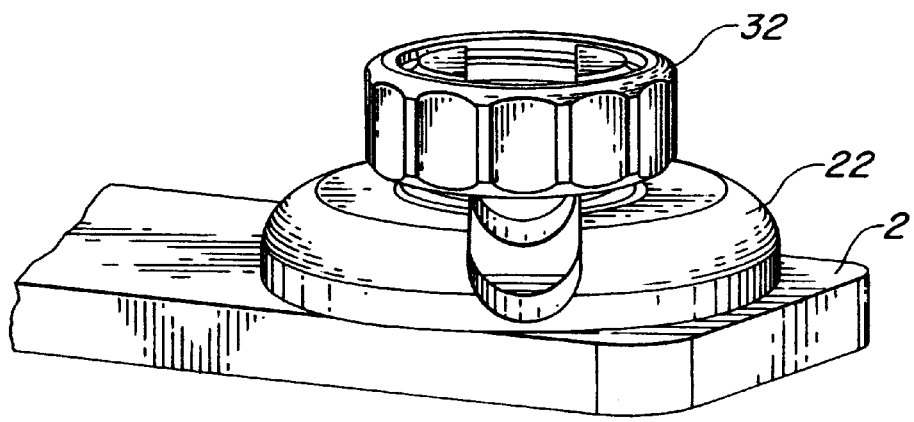
FIG. 2 shows elements of the embodiment of FIG. 1 seated on a plate.

FIG. 2 shows the platform 22 resting in position on the plate 2, with the bolt 12 omitted for clarity. As shown, the thickness of the support platform 22 constitutes a substantial structural reinforcement of the plate anchoring area. The groove in the platform member may taper inward slightly toward its base so that when the rod 3 is inserted in the slot and clamped downwardly, it wedges or fits closely against the sides of the supporting groove, adding rigidity to the overall system. The overall length of the bolt 12 is preferably such that the threaded portion extends only slightly, for example, less than a centimeter, above the top of the platform 22 to accommodate the nut 32, and the nut thus resides with a low profile over the rod and plate once it has been installed.

Figure 11:
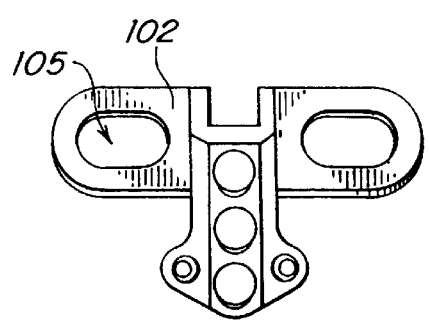
FIG. 11 shows one occipital fixation plate for use in an assembly of the present invention.

FIG. 11 shows by way of example one occipital fixation plate 102 for use with the present invention. Plate 102 includes two apertures 105, each of which accommodates a slotted bolt assembly, which may be any of the embodiments shown in the figures herein or their equivalents. As shown, for the occipital plate 102 the apertures 105 are elongated in the lateral direction to allow adjustment of bolt position in a side-to-side direction before tightening down to secure a rod, cable or other fixation linkage.

Figures 11A, 11B:
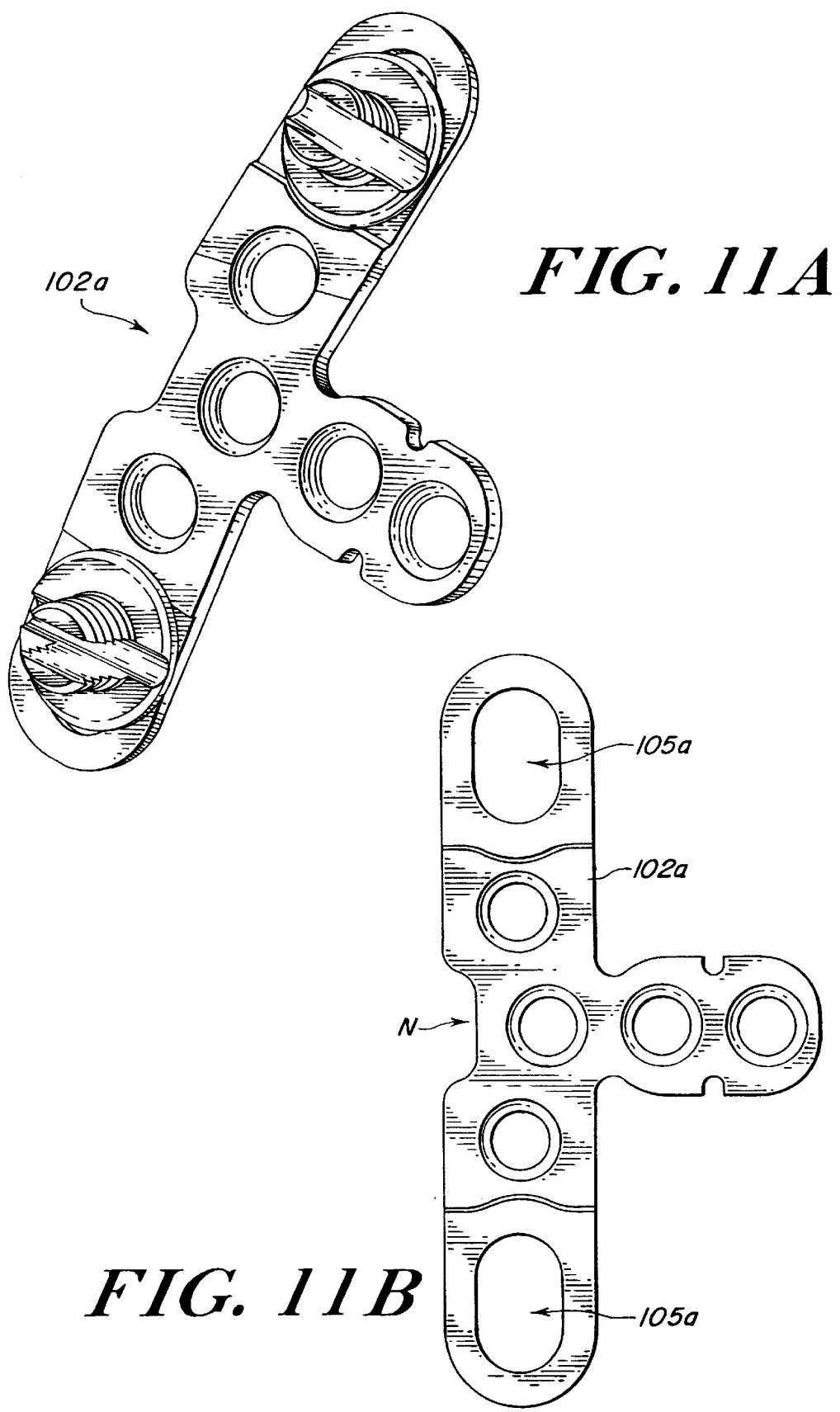
FIGS. 11A–11B show another occipital fixation plate.

FIGS. 11A–11B show a top perspective view and a top plan view, respectively, of another occipital fixation plate 102a for use with the present invention. Plate 102a, like plate 102, is T-shaped and includes two apertures 105a, one on each arm of the T, to accommodate slotted bolt anchor assemblies as discussed above for the apertures 105. The apertures 105a, elongated in the lateral direction to allow adjustment of bolt position in a side-to-side direction before tightening down to secure a rod, cable or other fixation linkage. Three chamfered holes extend along the midline for bone screws, and one additional bone screw opening is provided on each side arm to firmly fasten the plate against the occiput. The arms of the plate may curve, or extend at a slight dihedral angle to the central line of the T to conform to the skull.

Figure 12A:
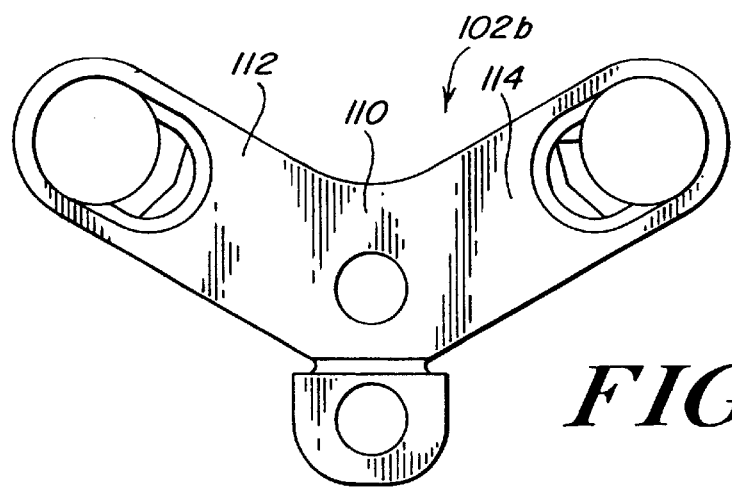
FIGS. 12A–12C illustrate another occipital fixation plate.
Figure 12B:
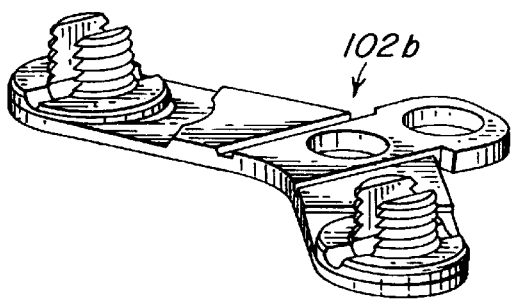
Figure 12C:
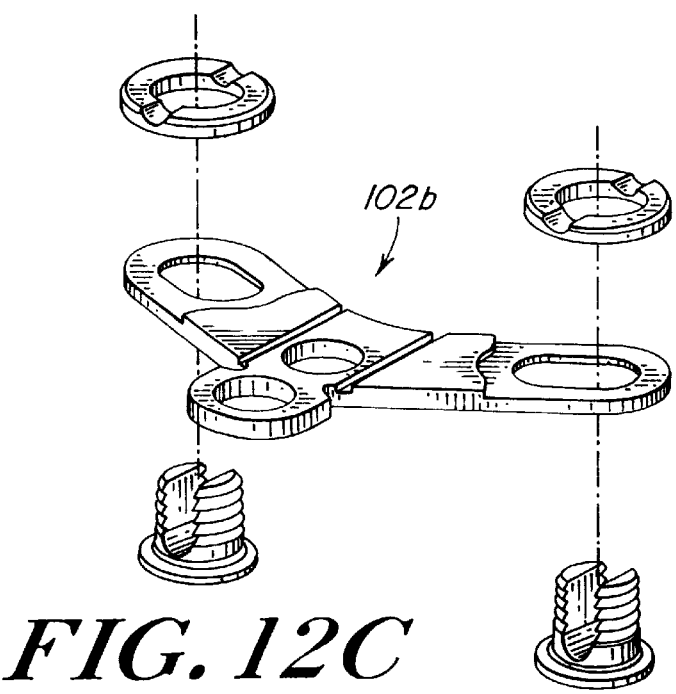
Figure 12D:
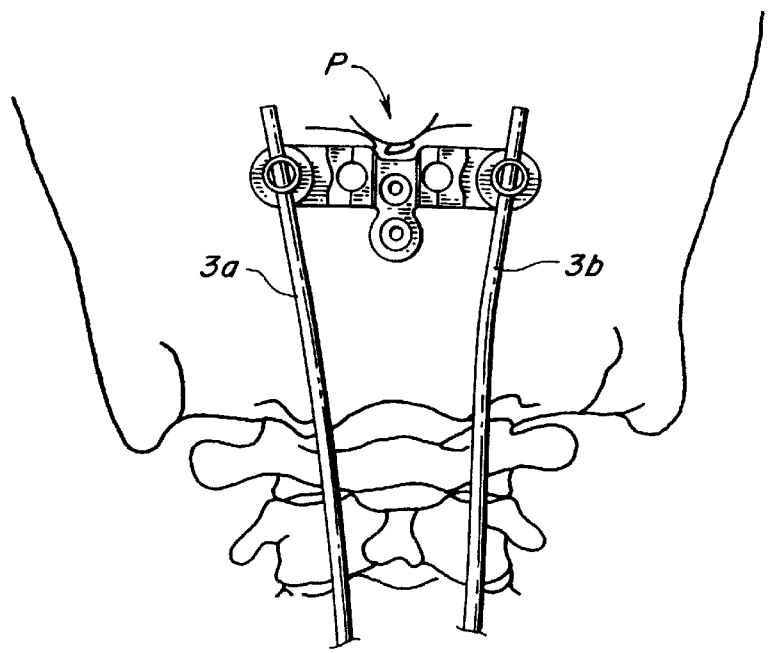
FIGS. 12D and 12E illustrate positioning of the occipital plates of FIGS. 11 and 12A–C, respectively.

FIG. 12D illustrates positioning of the T plate in use. The midline notch N (FIG. 11B) on the superior aspect of the plate is aligned with and positioned below the external occipital protuberance P of the skull, and aligned along the superior nuchal line. This positions the openings for the bone screws along the thickened internal central line of the occiput, assuring a stronger anchor.

Figure 5:
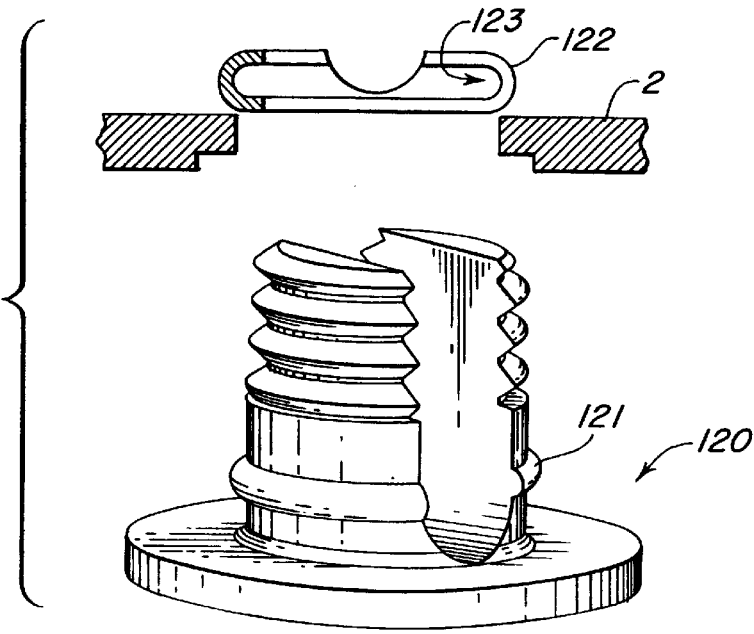
FIG. 5 illustrates another embodiment of an anchor bolt and support washer in accordance with the invention.
Figure 5A:
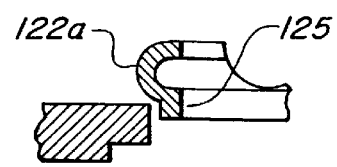
FIG. 5A illustrates another embodiment of a support washer.

The construction described above, wherein a bolt and swaged support washer assembly captures the plate, thus forms a conveniently installed one-piece plate and anchor assembly of versatile angulation for securing a fixation rod. In addition, the invention contemplates other embodiments. FIG. 5 illustrates one such embodiment, wherein an anchor bolt 120 is formed with a protruding circumferential ridge 121 positioned to capture the support washer 122 in a unitary assembly. The support washer 122 in this case has a corresponding groove or recess 123 into which the ridge fits to lock the washer onto the bolt and capture the plate 2. This grooved support washer may have a somewhat lower profile than that illustrated in FIGS. 1–3. Further, it need not have a structural portion corresponding to the dependent sleeve portion 24b of the first-described embodiment, although such a portion may be provided as a centering collar or sleeve 125 shown in FIG. 5A for the support washer 122a.

Figure 6:
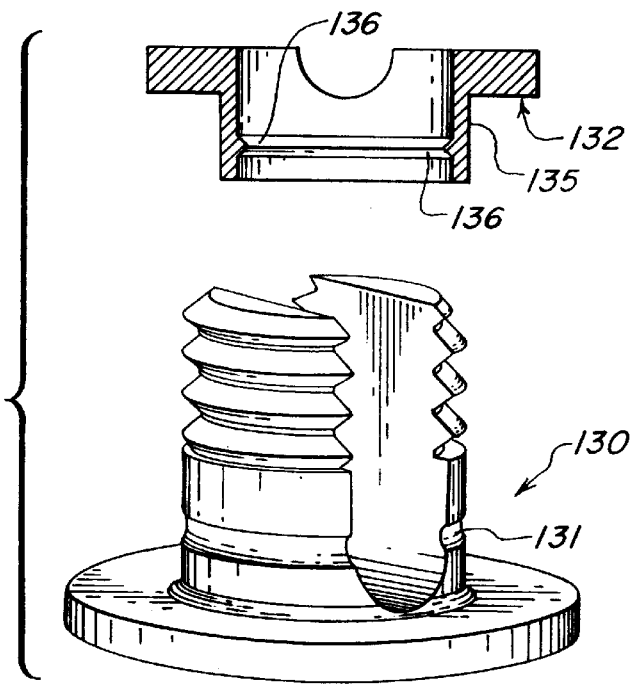
FIG. 6 shows another embodiment of an anchor bolt and support washer in accordance with the present invention.

FIG. 6 shows another embodiment of an anchor bolt and support washer 130, 132 in accordance with the present invention. As with the other embodiments, the two pieces fasten together to capture the bone plate and provide a nonseparating and unitary assembly that may be freely manipulated during installation, and that allows the slotted bolt to be adjusted in angle, and in some embodiments also in linear position, prior to tightening down of the bolt over the rod or cable linkage assembly. In the embodiment of FIG. 6, the bolt 130 possesses a recessed circumferential groove 131, and the support washer 132 has a corresponding portion with a protruding ridge 136 that snaps into the groove 131 to retain the two parts together. Ridge 136 need not be a continuous ridge, but may consist of one or a small number of slight bumps or protrusions which are sized to allow movement into the groove 131 with a slight pressure, and without shearing or cracking of the contacting parts. When bumps rather than a ridge are provided, the groove 131 may also be replaced by a few discrete indentations, in which case the indentations and bumps may further be positioned at angles selected to align the bolt slot with the rod support groove. A dependent collar portion 135 allows the mating ridge 136 or protruding bumps to be positioned quite low on the bolt shank, so that the device has an overall profile that extends only slightly above the plate to which it is mounted.

Figure 7:
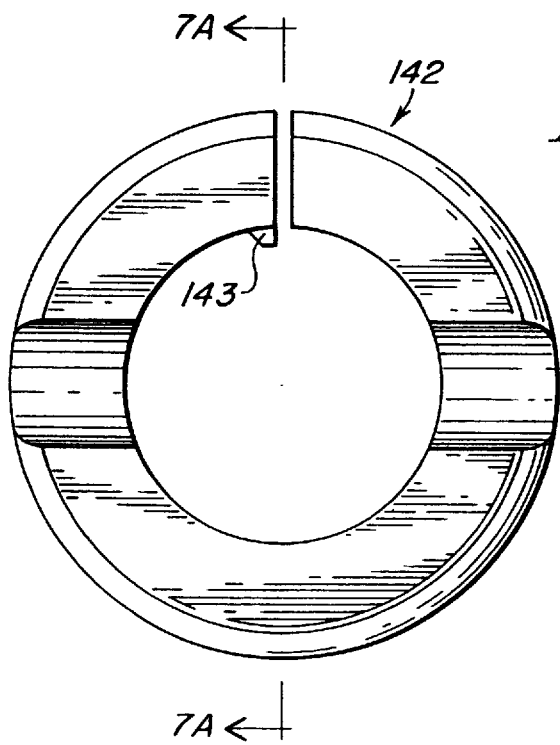
FIGS. 7–7B illustrate another embodiment of a support washer for the practice of the present invention.
Figure 7A:
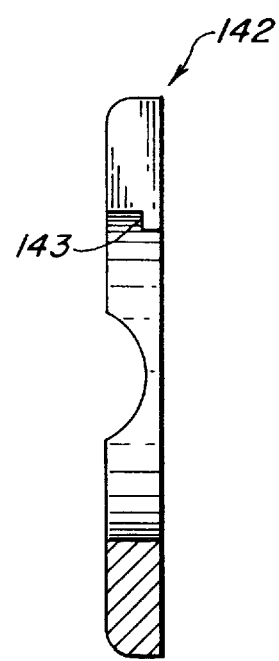
Figure 7B:
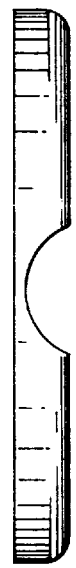
Figure 8:
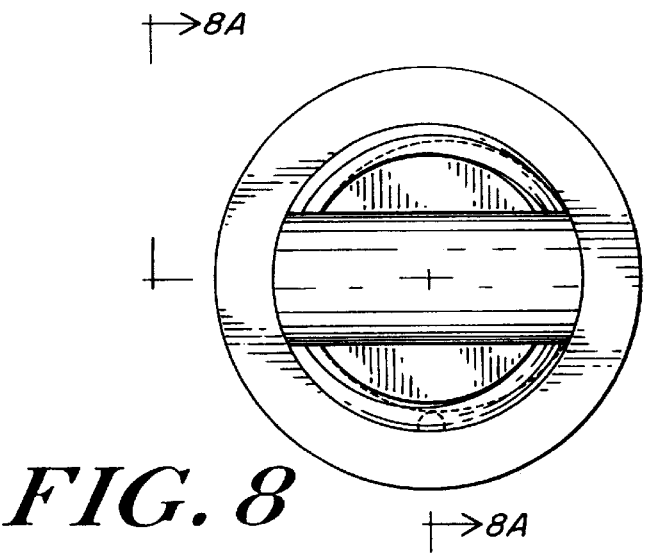
FIGS. 8–8A illustrate an anchor bolt of the present invention for use with the support washer embodiment of FIGS. 7–7B.
Figure 8A:
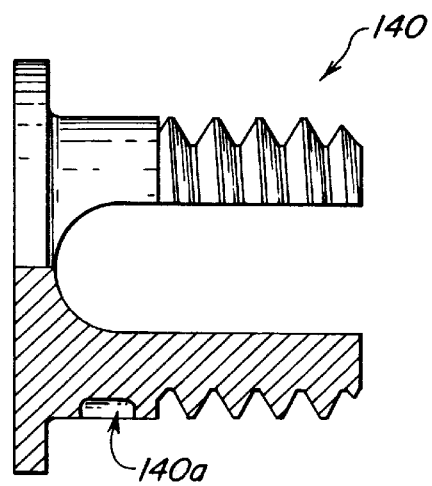
Figure 9:
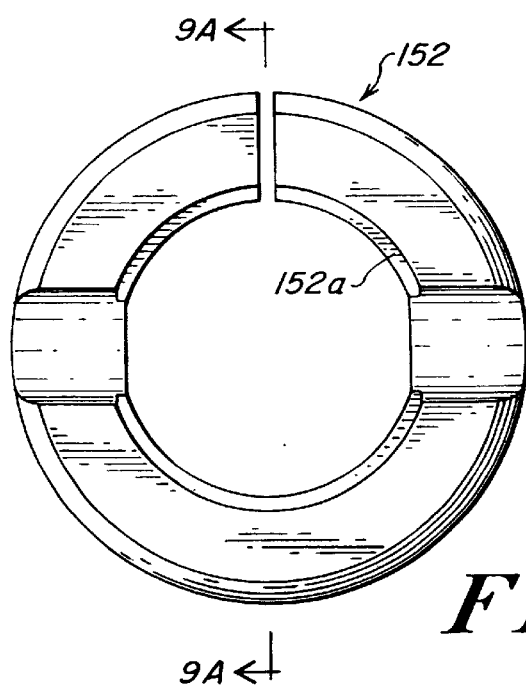
FIGS. 9–9B illustrate another embodiment of a support washer assembly of the present invention.
Figure 9A:
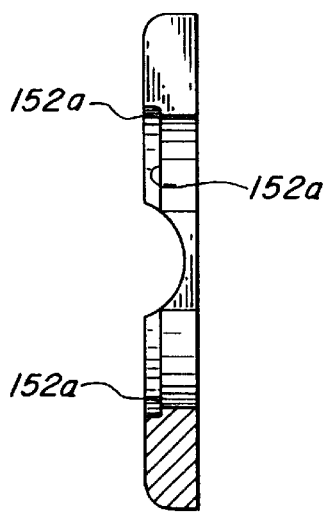
Figure 9B:
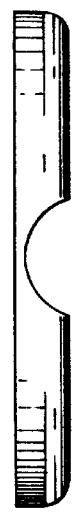
Figure 10:
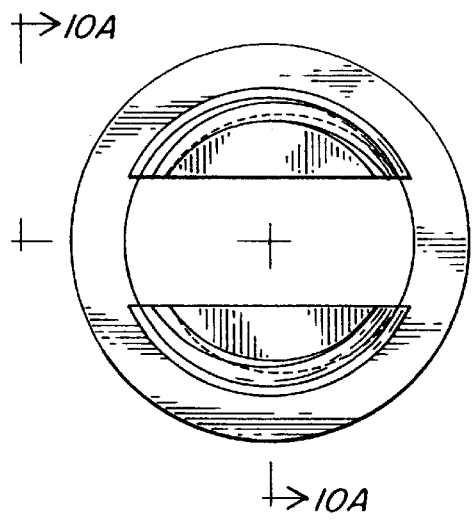
FIGS. 10 and 10A illustrate an anchor bolt embodiment for use with the washer assembly of FIGS. 9–9B.
Figure 10A:
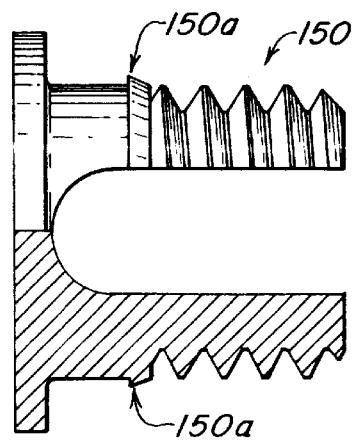

FIGS. 7–7B and 8–8A illustrate another embodiment of an orthopaedic anchor bolt 140 and support washer 142 for the practice of the present invention. As with the other embodiments, the washer has a transverse groove or seating surface for supporting the fixation rod or cable, and has a generally flat washer-like body that rests against the underlying bone plate. In the embodiment of FIG. 7 the washer 142 is preferably a split washer having a radially extending gap 142a that allows the washer to flex open and be placed over the bolt 140 such that a tooth 143, which projects radially inward, engages a corresponding recess 140a in that bolt. FIG. 7 shows the washer in a top plan view, while FIG. 7A illustrates a vertical section taken along a diametral plane and through the washer gap 142a. FIG. 7B shows a side plan view, illustrating the flat upper and lower surfaces of the washer. FIG. 8 is an end view of the bolt, 140, taken along the axial direction from above the slot of the bolt, with a dotted section line illustrated by A—A showing the direction of the partial cut away sectional view of FIG. 8A. As shown in FIG. 8A a recess 140a approximately one millimeter deep is provided in the bolt shank to capture the protruding tooth 143 of the support washer.

FIGS. 9–9B, 10 and 10A illustrate another embodiment of an anchor bolt and washer assembly 150, 152 of the present invention. These views correspond to those of FIGS. 7–7B, 8 and 8A, with similar features appearing similarly in the two figures. In this embodiment, however, bolt 150 is provided with a catch or radially-protruding and sharply angled edge 150a extending radially outward near the top of the shank portion of the bolt. The catch 150a catches the radially inward edge 152a of an upper surface of the support washer 152. For this purpose the radially inner region of the support surface is recessed slightly in the axial direction, so that the fastening edge 152a of the support washer 152 is lowered, at the level of the shank of the bolt 150. The entire assembly therefore has a low profile. The recessed inner step also protects the fastening edge from becoming nicked, rounded or otherwise impaired if a bulk finishing process such as tumbling, is employed to deburr or finish the support washer.

Thus, the anchor assembly may be implemented with a number of different possible washer or collar-like support elements to capture the plate and provide a freely oriented anchor bolt assembly. The plate itself may take varied forms, including individual vertebra plates, hooks or offset elements, or may be shaped like an occipital T-plate, forming an assembly with one or more anchor bolts.

It will be understood that in providing fixation rods to effect spinal alignment, fixation and fusion, the rods themselves and the rod-securing bolt assemblies 12, 22, 32 protrude upward from the bone, and closure of the surgical wound requires that surrounding soft tissue be closed and sutured over these projecting assemblies. For elderly and other patients whose tissue lacks sufficient elasticity, this may be difficult to achieve.

This problem is addressed in a further aspect of the invention by providing a Y-shaped occipital fixation plate that fastens in an inverted orientation and positions anchor bolts 12 lower down the skull, e.g., below the inferior nuchal line and in a position where the soft tissue is substantially thicker and better able to stretch and cover the mechanical components of the implanted assembly. FIGS. 12A–12C illustrate such a Y-shaped occipital fixation plate 102b.

Figure 12E:
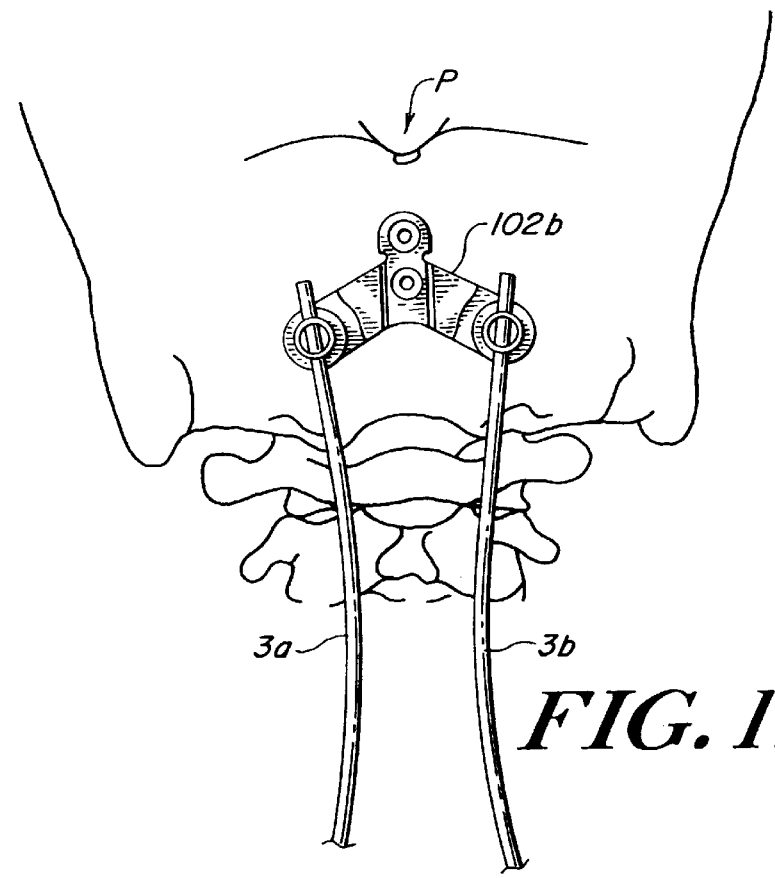

As shown in FIGS. 12A–12C, the plate 102b has first and second branch arms 112, 114 of the Y that extend to both sides of a central portion 110, and each arm is adapted, as described above, to receive a rod anchor bolt. In one preferred construction and method of use, the central portion 110 of the Y-plate forms a short central trunk, and the plate is located and secured in an inverted orientation as shown in FIG. 12E, with the Y-arms extending downwardly and out from the trunk, in an inverted Y position. The central trunk extends upwardly along the midline toward the exterior occipital protuberance P. The exterior occipital protuberance and the posterior margin of the foramen magnum may be used as a guide to the midline of the occiput, and the inverted Y-plate is positioned midway between these two landmarks, typically about one to one and a half centimeters below the exterior occipital protuberance. This places the rod anchor bolts several centimeters or more lower than occurs with the T-plate positioned as shown in FIG. 12D. When installed in this position, the anchor bolts are more dependably couched in a thicker bed of soft tissue, facilitating surgical wound closure, particularly for wasted or elderly patients having very little or very inelastic skin and soft tissue over the skull.

This completes a description of a number of representative embodiments of various anchor plates and the anchor bolt structures for orthopedic fixation in accordance with the present invention. As indicated above, one of ordinary skill in the art will readily appreciate that similarly shaped plates may be used as well. For example, plates characterized as having a V-, U-, or rotated C-shape may be used as well to provide lateral offset positions for rod-anchoring bolts in appropriate positions vertically offset from the occipital protuberance.

While not specifically illustrated, the aperture 5 in the plate may be a circular hole, or an elongated hole or may be an open-ended or a closed-ended slot. In the latter three cases, the bolt 12, in addition to being fully rotatable about its axis, may slide to an arbitrary linear position along the slot before it is tightened in position. The upper surface 13a of the base of the bolt (FIG. 1), as well as the lower surface 24a of the support platform (FIG. 3), may be toothed, knurled, roughened or otherwise textured to assure that these surfaces grip the plate when tightened and prevent the bolt from rotating or shifting position. Alternatively, or in addition the corresponding contact region of the plate may have such a gripping texture or surface finish. Furthermore, the plate component may have plural openings, grooves or channels adapted to receive one or more bolt/collar assemblies of the invention, and may have several grooves extending along different directions to provide a range of position options. The bolt and support plate may also be secured to each other by detents or interference fit, in variations of the configurations illustrated in the figures.

The occipital plate may be used with fixation rods that may have either a fixed diameter, or may have different diameters at different portions along their length (e.g., transition rods with multiple or stepped-diameter, transitioning from a four millimeter diameter at the thoracic vertebrae to three millimeter diameter in the cervical/cranial region). To fix the upper spine and relieve compression or stabilize the vertebrae for fusion, systems of the invention may also employ one or more cables (e.g., sublaminar cables to support the cervical vertebrae), which are applied between the rods to secure the transition rods to the spine.

Figure 13B:
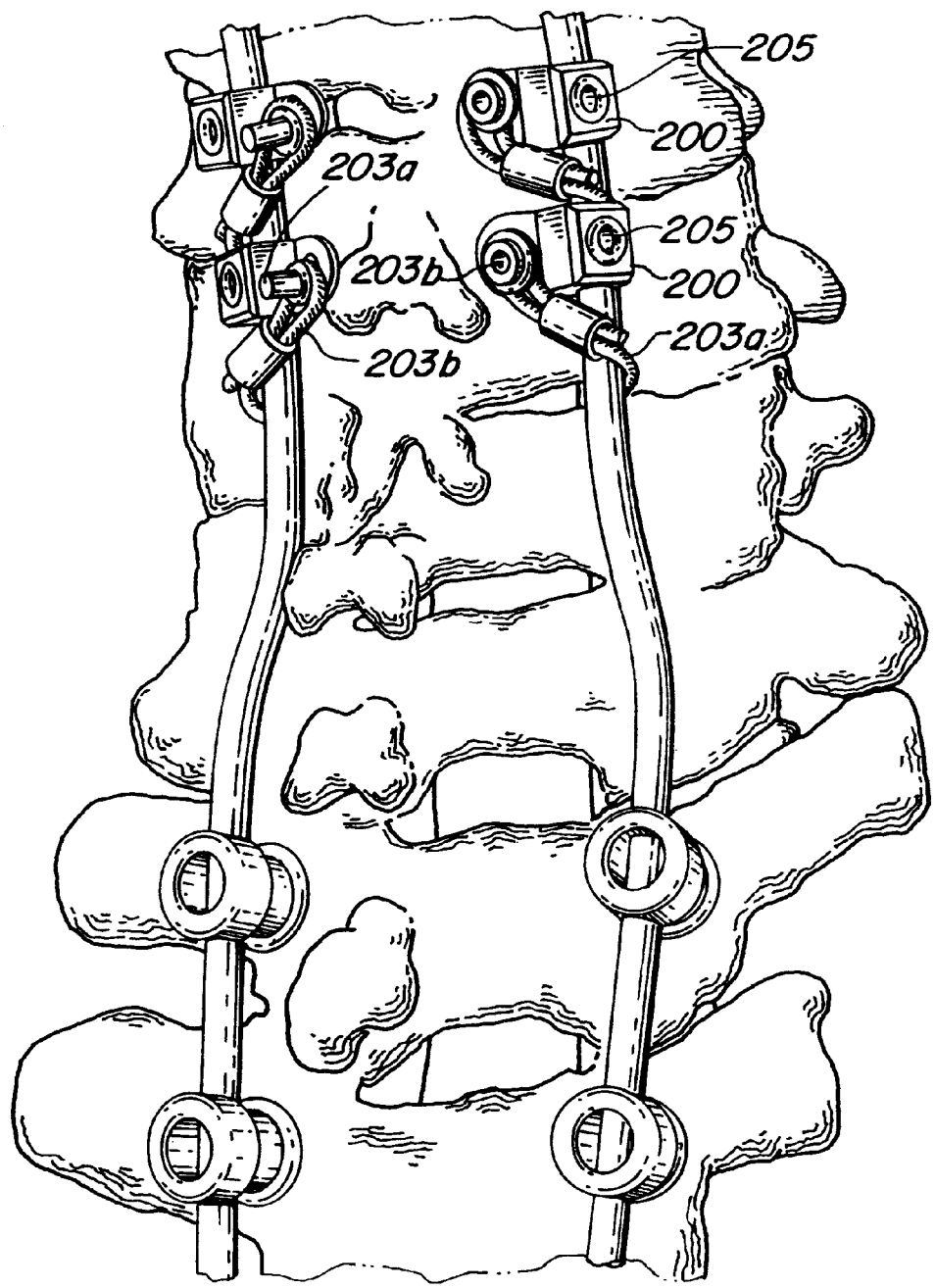
FIGS. 13A and 13C illustrate a cable connector and its use in a method of spinal fixation according to a system of the invention.

In accordance with one aspect of the invention, applicant provides a new cabling system with a cable connector mechanism 200 as shown in FIG. 13A configured to clamp onto a fixation rod and form a rigid, but selectively positioned, cable anchor. The cable connector 200 has a channel 210 sized to fit onto the fixation rod 3 (FIGS. 1, 13B), and a set screw 205 that tightens down to clamp against the rod 3 and secure the connector 200 in a desired, fixed position on the rod. As illustrated, the channel 210 is open on one side, and its contour is rounded such that the rod seats low against the contour of the floor of the channel. As a result, when the set screw 205 is tightened. the rising wall or step region S of the body prevents any lateral motion of the rod. The cable connector 200 also has a lateral flange 208 extending out from the channeled body, with an eyelet, or aperture or bolt hole 206 through which a cable is secured. The aperture 206 thus provides a fixed point for vertebrato-rod cabling.

With this construction, an occipital plate, such as a T-, Y- or inverted Y-plate 102a or 102b is installed, several vertebra anchor screws are placed, and the rods 3 are contoured and fitted into position between the slotted anchors of the occipital plate and the anchor screws attached to the vertebrae. In addition, one or more cable connectors 200 are fitted onto the rod and cables are laced to one or more vertebrae, tensioned and fastened to the connectors to firmly secure the rod to the cervical spine, binding and supporting specific vertebrae. The connectors 200 provide fixed anchor points for the cables at the level of the vertebra, resulting in more secure fixation. In particular, they provide fastening such that the cable has relatively short spans that do not allow a supported vertebra to shift appreciably, and the cable itself is not free to shift vertically. FIG. 12F illustrates sublaminar threading of Songer cables, which is preferably carried out at each of the vertebrae to be supported, before installation of the rods 3a, 3b, as described further below.

The fixation system may be installed as follows. When cabling is to be used for fixation of the cervical (or other) vertebrae, the cables may initially be inserted at all levels to be fused. Advantageously, by using titanium double cables with a leader, two cables may be applied simultaneously at each vertebral level using one sublaminar passage. For Songer cables, the procedure may be effected by contouring the double cable leader in a C-shape conforming to the specific anatomy. Starting caudally, the contoured leader is introduced inferiorly, beneath and around the relevant lamina. As it emerges on the superior side, the leader is caught with rubber-clad forceps or a blunt hook and pulled upward to maintain tension on the cable. This minimizes contact with the underlying dura. The leader is then cut and the cables are separated laterally and clamped at each side of the wound using rubber-clad forceps. The process is repeated sequentially at all levels to be fused, resulting in a set of cable segments 230 as shown in FIG. 12F. The segments are labeled (a)–(h) to more clearly depict the left and right sides of each cable.

The two rods 3a, 3b are then contoured and are cut, if necessary, to assure a precise anatomical fit, and their upper and lower ends are captured in the anchor bolts of the occipital plate and the vertebral anchor screws, respectively, bilaterally. Final tightening of the slotted anchor bolts is performed later, after the cables are securely in place.

Once the rods are loosely secured, the inferior cable ends at each level are placed to the outside of each rod. Beginning with the most distal cable, the leadered end is passed through the eyelet 206 of a cable connector 200, and through a cable eyelet (formed by crimping ferrule about a looped end of a cable) and finally draped over the side. The connector 200 is then placed on the rod 3a or 3b, and loosely secured by tightening the set screw 205. This procedure is repeated, providing one cable connector for each cable; the connector is loosely secured to one of the rods at each level. The cables are then tensioned and crimped, and the cable connectors 200 are each tightened down onto the rods. Final tightening of the fixation rods in their anchor bolts may then be effected. FIG. 13b illustrates a model spine with two cervical vertebrae cabled in this manner.

FIG. 13C is an enlarged line drawing illustrating details of cable attachment to cable connector 200. As shown, a cable 300 has its leader end 301 inserted through the eyelet 206 of a cable connector. A cable eyelet or end-loop 311 of a different cable 310 (or the other end of the same cable according to some methods) is passed over the leader 301 and nested down against the surface of the connector 200, and a top-hat crimp termination 305 is used to secure the leader end. The crimp termination 305 has a brim 306 that is of greater diameter than the loop opening of cable eyelet 311, and also greater than the connector eyelet 206. The crimp termination also has a cylindrical body 307 through which the leader has been fitted, and this is crimped, or loosely set, once the two ends 301, 311 have been positioned at the connector 200, so that both cable ends are captured at the connector. As described above, the cable connector assembly is fastened to one of the fixation rods 3a, 3b during a multi-step procedure in which the cables then rods, then cable connectors are positioned. A tensioning tool (not shown) then tensions each cable by pulling the leader 301 (e.g., gripping the leader and pushing against the termination) while crimping the body portion 307 of the top hat termination securely on the cable leader end 301 for final tensioning once the cables and other components have been aligned, attached and undergone preliminary tightening. The loops 311 may be preformed (e.g., the cables as shown in FIG. 12F may be shipped ready to use with one straight and one looped end), or the loops may be formed during the procedure, by crimping a sleeve or ferrule over the cable 310 and its looped-back end 310a to form the cable eyelet 311.

It will be understood that the use of cables to secure the rods to vertebrae has been a generally accepted practice in situations where additional support is necessary without using anchor screws in the affected vertebrae. However, it will be understood that rather than passing a sublaminar cable about the vertebra, it is also possible to place relatively small anchor screws in the cervical vertebrae for directly clamping to the fixation rod. In this case a so-called mini-polyaxial screw (Depuy Acromed part Nos. 1746-07-408 to −450 or 1746-07-508 to 550), similar in overall structure to a standard Moss-Miami screw, may be used together with a suitable fixation rod assembly.

Figure 4:
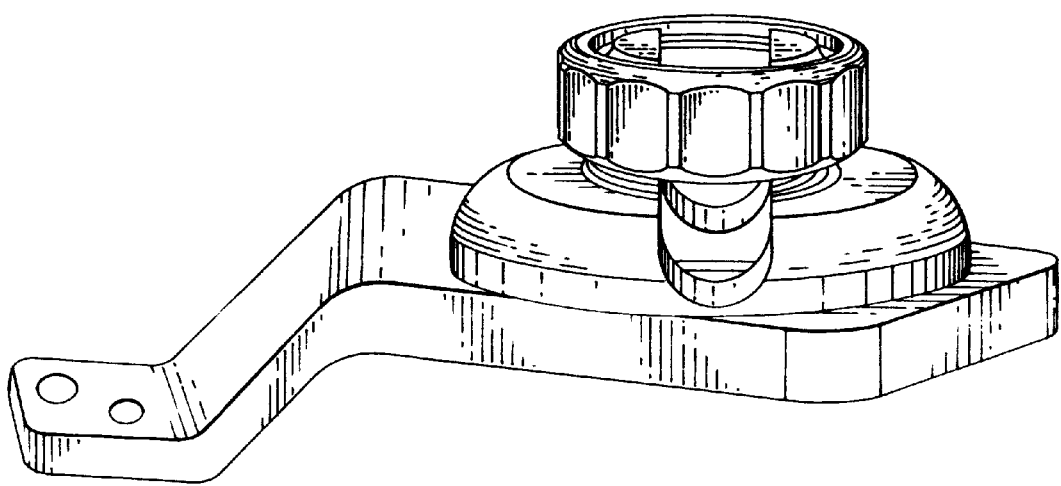
FIG. 4 illustrates an offset tab embodiment.

Anchor plates of the invention have particular utility in an occipital fixation assembly, wherein the plate portion is shaped to firmly seat against the occiput. The ability to conveniently provide a complete rotation of the slotted rod anchor bolt while allowing some translation or offset is of great utility in minimizing misalignment of the transition rod and avoiding the application of unwanted pull-out forces on the anchor screws. However, the constructions of the invention also have utility in diverse other embodiments, wherein the plate portion of the assembly is configured in various lengths or shapes, such as an offset tab embodiment as shown in FIG. 4, short vertebra plates, and other shapes adapted to specific applications.

In the various embodiments of occipital plates described herein, the plate itself is configured to anchor to the skull along the midline of the occiput, where bone is thicker and presents a stronger substrate for anchoring, and to secure fixation rods along the branches or arms of the occipital plate adjacent to the anchor screws. Advantageously, the inverted Y-plate embodiment positions the rod-securing slotted bolts or cap assemblies below the nuchal line, where the presence of sufficient or thicker soft tissue ensures that wound closure may be effected without excessive stretching or stress. The invention may alternatively achieve this result with plate shapes such as a V or other shape.

The invention being thus disclosed and illustrative embodiments depicted herein, further variations and modifications of the invention, will occur to those skilled in the art, and all such variations and modifications are considered to be within the scope of the invention, as defined by the claims appended hereto and equivalents thereof.

What is claimed is:

1. An anchor assembly for spinal fixation, comprising:
    an anchor plate having a central trunk and first and second arms extending outwardly and inferiorly to the trunk, the anchor plate being configured to be attached to bone below a patient's external occipital protuberance and below the inferior nuchal line;
    at least one bolt fixed to at least one of the first and second arms, the bolt having a slot configured to capture and clamp a fixation member, the bolt being freely rotatably with respect to the anchor plate before fixation member clamping.

2. The anchor assembly of claim 1, wherein a first bolt is affixed to the first arm and a second bolt is affixed to the second arm.

3. The anchor assembly of claim 1, wherein the central trunk is configured to be attached to bone.

4. The anchor assembly of claim 3, wherein the central trunk includes at least two apertures and at least two bone screws for fixing the anchor plate to bone through the apertures.

5. The anchor assembly of claim 1, wherein the anchor plate includes at least one elongated aperture on at least one of the first and second arms, a bolt being adjustably positionable along the length of the elongated aperture before clamping.

6. The anchor assembly of claim 1, further comprising a support platform, wherein the support platform is configured to slide over the bolt to capture the anchor plate between the bolt and the support platform.

7. The anchor assembly of claim 6, wherein the support platform comprises a split washer for mating with a catch or detent on the bolt.

8. A spinal fixation system comprising:
a first anchor element in the form of an occipital plate having a central trunk and first and second arms extending outwardly and inferiorly to the trunk, the occipital plate being configured to be attached to bone below a patient's external occipital protuberance and below the inferior nuchal line, the first anchor element having at least one anchor screw hole disposed therein and at least one bolt-receiving aperture disposed therein;
at least one anchor bolt seated in the bolt-receiving aperture of the first anchor element, the bolt having a slot extending transversely through a portion thereof; and
a linking member having a proximal end portion clamped in said slot and having a distal end anchorable to a patient's vertebral body.

9. The system of claim 8, wherein a first bolt is affixed to the first arm and a second bolt is affixed to the second arm and a first linking member is clamped in a slot in the first bolt and a second linking member is clamped in a slot in the second bolt.

10. The system of claim 8, wherein the central trunk is configured to be attached to bone.

11. The system of claim 10, wherein the central trunk includes at least two apertures and at least two bone screws for fixing the anchor plate to bone through the apertures.

12. The system of claim 8, wherein the first anchor element includes at least one elongated aperture on at least one of the first and second arms, the bolt being adjustably positionable along the length of the elongated aperture before clamping.

13. The system of claim 8, further comprising a support platform, wherein the support platform captures the anchor plate between the bolt and the support platform.

14. The system of claim 8, wherein the support platform comprises a split washer for mating with a catch or detent on the bolt.

15. The system of claim 8, further comprising at least one cable connector fixable to the linking member in a predetermined position and at least one cable attached to an eyelet in the cable connector and fixable to a patient's vertebra.

16. The system of claim 8, wherein the system is configured to clamp the linking member in the slot below a patient's inferior nuchal line.

17. A method for occipital coupling of a spinal fixation element, comprising:
a) providing a spinal fixation element having a proximal end and a distal end and fixing the distal end to a patient's vertebrae;
b) providing a first anchor element in the form of an occipital plate having a central trunk and first and second arms extending outwardly and inferiorly to the trunk, and attaching the occipital plate to a patient's bone below an external occipital protuberance and below an inferior nuchal line, the first anchor element having at least one anchor screw hole disposed therein for attaching to the patient's bone and at least one aperture having a bolt therethrough, the bolt having a base and a shank extending through the aperture, the shank having a slot for receiving the spinal fixation element; and
c) coupling the proximal end of the spinal fixation element to the slot.

18. The method of claim 17, wherein the proximal end of the spinal fixation element is coupled to the slot below the inferior nuchal line.

19. A cable connector system for coupling a spinal fixation rod to a vertebral body, comprising:
a body having a generally elongated channel extending therethrough sized to receive a spinal fixation rod therein, the channel being open sided such that the body may be placed from a side onto a fixation rod at a selected position while the rod is at least partly anchored in position, the body further having an eyelet portion adapted to receive a cable;
a clamping screw fitted in the body adjacent the channel for locking the spinal fixation rod and securely fixing the position of the body on the spinal fixation rod;
a cable passing through said eyelet for securing a vertebral body to the body and thereby securing the vertebral body to the spinal fixation rod.

20. The system of claim 19, wherein the cable includes a leadered end and an eyelet wherein when the cable is laced to a vertebra, the leadered end passes through the cable connector body eyelet and through the cable eyelet for securing the cable to the cable connector body, and the vertebra to the spinal fixation rod.

21. The system of claim 20, further comprising a crimping element crimped onto the cable where the cable has passed through the cable eyelet to fix the cable to the cable connector body.

22. The system claim 19, further of comprising a plurality of cable connector and a plurality of cables, each cable having a leadered end and an eyelet, wherein a leadered end of a first cable passes through a cable connector body eyelet of a first cable connector and a cable eyelet of a second cable for fixing the first and second cables to the first cable connector.

23. The system of claim 22, further comprising a first crimping element crimped onto the leadered end of the first cable where the cable has passed through the eyelet of the second cable to fix the first and second cables to the first cable connector.

24. The system claim 19, wherein the body further comprises a lateral flange and the eyelet is provided on the flange.

* * * * *